US006268349B1

(12) United States Patent
Hirschman

(10) Patent No.: US 6,268,349 B1
(45) Date of Patent: *Jul. 31, 2001

(54) METHOD FOR TREATING B19 PARVOVIRUS INFECTIONS

(75) Inventor: Shalom Z. Hirschman, Riverdale, NY (US)

(73) Assignee: Advanced Viral Research Corp., Hallandale, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/837,988

(22) Filed: Apr. 15, 1997

(51) Int. Cl.[7] .......................... A01N 61/00; A01N 43/04; C12Q 1/70; G01N 33/53
(52) U.S. Cl. ..................... 514/44; 514/1; 514/2; 435/5; 435/6; 435/7.1; 435/7.2; 435/235
(58) Field of Search .......................... 514/1, 2, 44; 435/6, 435/7.1, 7.2, 5, 235

(56) References Cited

U.S. PATENT DOCUMENTS 5,449,608 * 9/1995 Young et al. .......................... 435/7.2

OTHER PUBLICATIONS

Reynolds, Margaret R., Generalized Vaccinia Successfully Treated With Lipoprotein–Nucleic Acid Complex (Reticulose), Archives of Pediatrics, 77:421–422, 1960.
Wegryn, Stanley P., Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia and Chicken Pox, J. Roy. Coll. Gen. Practit., 1970, 19, 182.
Cohen, Matthew, The Efficacy of a Peptide–Nucleic Acid Solution (Reticulose) for the Treatment of Hepatitis A and Hepatitis B—a Preliminary Controlled Human Clinical Trial, J. Roy. Soc. Health, Dec., 1992, 266–270.
Friedland, Bernard, In Vitro Antiviral Activity of a Peptide–Nucleic Acid Solution Against the Human Immunodeficiency Virus and Influenza A Virus, J. Roy. Soc. Health, Oct. 1991, 170–171.

Behbehani, Abbas M., Haberman Sol and Race, George J, The Effect of Reticulose on Viral Infections of Experimental Animals, Southern Medical Journal, Feb., 1962, 185–188.
Treatment of Viral Diseases with A Lipo–protein Nucleic Acid Complex (Reticulose)—A Clinical Study, Scientific Exhibit: Virginia State Medical Society Meeting, Washington D.C., Nov., 1957.
Kempe, Henry C., Fulginiti, Vincent A., and Vincent, Leone St., Failure to Demonstrate Antiviral Activity of Reticulose, Diseases of Children, vol. 103, No. 5, 655–657, 1962.
Sanders, Murray, Controlled Animal Studies with Reticulose Illustrating the Interference of Lipoprotein–Nucleic Acid Complex in the Experimental Animal Infected with Human Pathogenic Viral Entitities, Southern Medical Association Scientific Exhibit, Dallas, Texas, Nov., 1961.
Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–24, 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.
Medoff, Lawrence R., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Kosaka, K. and Shimada, Y., Infectious Hepatitis, Symposium, pp. 61–74, 1960.
Anderson, Robert H. and Thompson, Ralph M., Treatment of Viral Syndrome with a Lipoprotein–Nucleic Acid Compound (Reticulose), A Report of Five Cases, Virginia Medical Monthly, 84:347–353, 1957.

* cited by examiner

Primary Examiner—Jezia Riley
(74) Attorney, Agent, or Firm—Cohen, Pontani, Lieberman & Pavane

(57) ABSTRACT

The present invention discloses a treatment for patients with the B19 parvovirus associated symptoms or patients carrying or infected by the B19 parvovirus or having antibodies against the B19 parvovirus using Product R, a peptidenucleic acid preparation.

12 Claims, No Drawings

METHOD FOR TREATING B19 PARVOVIRUS INFECTIONS

BACKGROUND OF THE INVENTION

1. Field of the Invention

The present invention relates to a method for using Product R as hereinafter defined to treat patients infected with B19 parvovirus.

2. Description of the Related Art

Treatment of viral diseases in humans is a major focus of medical science. While some progress has been made, viral infections are still among the diseases most difficult to treat. Despite growing understanding of viral diseases along with improved techniques for detecting and treating them, few antiviral drugs have proved effective. Some viral diseases such as HIV are life threatening; others such as herpes simplex virus and influenza virus continue to cause severe problems. Further, new viral diseases constantly appear as an inevitable consequence of evolution. Thus, searching for a novel and effective way of treating viral diseases remains imperative and challenging.

Product R[1] emerged as an antiviral product in the 1930's. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

[1]. The agent is known under the trademark "Reticulose", a trademark of Advanced Viral Research Corp.

Despite these early promising clinical reports, systematic studies have rarely been performed to establish clinical utility. Optimum dosages of Product R for treating viral infections as indicated above have been poorly investigated. In fact, most of the clinical reports lacked necessary controls and statistically sufficient samples for evaluating the effectiveness of Product R. Note, two earlier publications challenged that Product R failed to demonstrated antiviral activity. In light of this controversy, the present status of the art of using Product R in treating viral infections remains questionable. Close examination of the development history of Product R reveals no meaningful pattern that could be followed to designate a treatment for a particular viral infection, for viruses causing those infections are extremely diversified in their genetic traits or/and pathogenesis. In addition, earlier clinical applications described Product R only as an agent to be administered alone. Product R has never been suggested to be applied in combination with other antiviral drugs; nor has Product R been administered for a period longer than about two months. Given the limits of prior art, developing new treatment strategies using Product R is desirable.

In developing an antiviral agent, it is well known that inhibitory activity of an antiviral agent against a particular virus cannot be equated with its inhibitory effect against another virus. For example, acyclovir has proved to be specifically effective against herpes simplex 1 and 2 but not against cytomegalovirus (CMV), even though both HSV and CMV belong to the same herpesvirus family, sharing certain genetic features. The specificity of acyclovir rests on the activity of the thymidine kinase gene unique to HSV 1 and 2, indicating that a distinctive feature of each individual virus forms a basis for developing an antiviral agent specifically against this very virus. In other words, treatment of a viral infection using a certain antiviral agent does not necessarily indicate that the same agent will produce the same effect when used for treating other viral infections. The genetic diversity of viruses further mandates that an attempt to be made to discern the effectiveness of a new application of an antiviral agent to a different virus.

An antiviral agent usually interacts with molecules involved in different stages of viral infections: in early events such as adsorption, penetration (internalization), and uncoating; in virus replication characteristic for each virus genome and components of the nucleoprotein complex; and in the chemistry of metabolic pathways. The best targets for inhibition by an antiviral agent are molecules serving a function unique to the virus, with no analogous counterpart in host cells. In order to identify the virus-specific molecule with which a putative antiviral agent interacts, it is important to characterize viruses in terms of particle and genome structure, as well as to define specific biochemical events that occur in infected cells. Although progress has been made in discovering molecules necessary for virus adsorption, replication and metabolism, current knowledge remains insufficient to explain many aspects of these events. Consequently, not every antiviral agent's function is fully defined in terms of its interaction with a target virus through one or a series of the indicated events; much less is understood where an antiviral agent is employed to treat a new viral infection, especially if the antiviral agent has been poorly characterized. Without the knowledge of a virus' genetic traits and the chemical properties of an antiviral agent, treatment of a viral infection becomes unpredictable.

SUMMARY OF THE INVENTION

The object of this invention therefore is to develop a method for treating a patient infected by B19 parvovirus, or exhibiting B19 parvovirus associated syptoms, or having antibodies to B19 parvovirus, by administering parenterally to the patient Product R, an antiviral agent composed of peptides and nucleic acids.

Parvoviruses have interested veterinarians because they are responsible for many serious diseases in animals. B19 Parvovirus, the only parvovirus known to be pathogenic in humans, was discovered in the mid-1970s during the course of investigating laboratory assays for hepatitis B.

Acute infection with B19 parvovirus causes the common childhood exanthem fifth disease (erythema infectiosum) characterized with "slapped cheek" facial erythema and a lacy, reticular, evanescent maculopapular eruption over the trunk and proximal extremities. Because parvovirus is extremely contagious, an epidemic may be recognized in the community. In a single patient, however, fifth disease is often confused with measles and other childhood exanthems.

While parvovirus infection in adults is most frequently asymptomatic or results only in a nonspecific flulike illness, adults with fifth disease more commonly suffer joint pains or frank arthritis than a rash. The patient's symptoms—including the distribution of joints affected, the presence of frank inflammation, and even a positive rheumatoid factor test—mimic rheumatoid arthritis. Postparvovirus arthropathy can persist for weeks, months, or even years. In one clinic 12% of patients with new arthritis had evidence of recent parvovirus infection. Acute parvovirus infection may also resemble fibromyalgia or systemic lupus erythematosus. Recently, evidence of chronic parvovirus infection has been found with necrotizing vasculitis resembling polyarteritis nodose or Wegener's granulomatosis.

In persons with underlying hemolysis, acute parvovirus infection causes transient aplastic crisis, an abrupt cessation of red blood cell production in the bone marrow, characterized by reticulocytopenia, absent erythroid precursors in marrow, and precipitous worsening of anemia. Temporary depression of erythropoiesis is probably a constant feature of acute parvovirus infection. Although suffering from an ultimatley self-limiting illness, the patient with aplastic crisis may be acutely ill. Symptoms may include not only dyspnea and fatigue resulting from severe anemia but also extreme lassitude, confusion, and congestive heart failure.

The pattern of disease that follows parvovirus infection is the result of balance between virus, marrow target cell, and the immune response. Bone marrow depression in parvovirus infection occurs early, during the viremia. Normally, infection is terminated by a neutralizing antibody response. The immune response produces the clinical manifestations of fifth disease, in children a rash illness and in adults a rheumatic syndrome; these symptoms are coincident with antibody formation and are immune-complex mediated. In both persistent infection in children and adults and in utero infection, failure to mount a neutralizing antibody repose allows parvovirus to persist and cause chronic anemia. Congenital infection is characterized by low-level infection of marrow, and the chronic anemia may be the result of indirect, perhaps immune-mediated, host responses.

B19 parvovirus has been recently reclassified within Parvoviridae in a new genus called Erythrovirus. Parvovirus genome is a linear, single-strand DNA. The parvovirus DNA replication takes place in the cell nucleus. The location of replication, combined with the fact that the cell is required to go through S phase in order for replication to occur, suggests a very close relationship between viral and cellular replication. As a characteristic for B19 parvovirus and the other vertebrate parvovirus, only a single strand is used for coding genes. Unlike other parvoviruses, B19 parvovirus has the longest terminal repeats among the parvoviruses, 365 nucleotides. For B19 parvovirus the 5'- and 3'- ends have identical sequences. The length; the presence of several long, direct repeat sequences, the high content of guanosine/cytosine pairs; and the resulting strong secondary structure of the B19 parvovirus terminal repeat sequences have made them resistant to molecular cloning in bacteria. Both the positive and negative viral strands of B19 parvovirus are replicated and packaged.

Although the scheme of DNA replication of B19 parvovirus is broadly similar to that of other autonomous parvoviruses, the pattern of RNA transcription sets it apart from most of the other Parvoviruidae. B19 parvovirus transcription is unusual in 1) the large number of transcripts, 2) the extent of splicing and large size of the introns removed, 3) the failure to coterminate all transcripts at the far right side of the genome, 4) the use of unusual polyadenylation signals for termination of transcripts in the middle of the genome, 5) the use of a single strong promoter at the far left side, with an accompanying leader sequence to initiate transcription of all RNA species.

B19 parvovirus is remarkable for its extremely narrow tropism. The narrow tissue or species specificity of parvoviruses is one of the most interesting aspects of the family. Productive infection has only been demonstrated in human erythroid progenitor cells. The major site of viral replication in patients has been assumed to be the adult marrow and fetal liver, the site of erythropoiesis during development.

Viral tropism is the result of expression of its cellular receptor, erythrocyte P antigen or globoside, in only a few human tissues, and an intracellular block in transcription in nonpermissive cells.

The virus is cytotoxic to host cells through action of the nonstructural protein; abortive infection in cells that is not permissive to viral replication might nevertheless result in cell death.

Although treatments of persistent B19 parvovirus infections by administration of immunoglobulin has been reported, an effective treatment regimen has not been established. Further more, the known treatments of fifth disease and transient aplastic crisis are for relief of symptoms only.

It has now been discovered that Product R is useful in treating patients identified as having B19 parvovirus associated symptoms, as well as patients identified as infected by or carrying B19 parvovirus or having antibodies to B19 parvovirus. The present invention relates to a method for treating the identified patients by administering parenterally to the patients an effective B19 parvovirus treatment amount of Product R from about 5 microliters to about 40 microliters per kilogram of body weight per day in a sterile injectable formulation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE PRESENTLY PREFERRED EMBODIMENTS

The present invention discloses the use of Product R as a method of treating patients identified as having B19 parvovirus associated symptom(s) by administering parenterally an effective dose of Product R.

The invention also discloses the method of treating a patient infected by or carrying B19 parvovirus with Product R to inhibit the replication of the B19 parvovirus in infected patient cells and to prevent B19 parvovirus infection from developing in humans infected with the B19 parvovirus.

The invention further discloses the method of treating a patient carrying antibodies against B19 parvovirus by administering parenterally effective dose of Product R.

As used herein, Product R is the product produced according to either of the following methods.

Method I For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/100 ml, the final volume is approximately 5 liters. The pH is then adjusted with either concentrated HCl (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

For the above B19 parvovirus infections, whether the patient exhibits B19 parvovirus associated symptoms, infections or antibody responses, a suitable effective dose of Product R will be in the range of from about 5 microliters to about 40 microliters per kilogram of body weight per day, preferably in the range of about 10 microliters to about 25 microliters per kilogram of body weight per day. Most preferably Product R is administered in an amount of about 30 microliters per kilogram of body weight per day for about one week, followed by about 15 microliters per kilogram of body weight per day in a sterile injectable formulation until the patient becomes asymptomatic or viral load becomes undetectable. The desired dose may be administered as two, three or more sub-doses at appropriate intervals, generally equally spread in time, throughout the day. Preferably, the full daily dose is administered in one administration.

Product R may be administered by any suitable injection route including, but not limited to intravenously, intraperitoneally, subcutaneously, intramuscularly, and intradermally, etc. The presently preferred route of administration is intramuscularly. It will be appreciated that the preferred route may vary with, for example, the condition and age of the recipient.

Product R may be used in therapy in conjunction with other medicaments including corticosteroid, gamma globulin, glucose, or vitamins, antiviral agents such as interferon or interleukin, etc.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method of treating a patient having B19 parvovirus associated symptoms, comprising administering parenterally to said patient an effective B19 parvovirus treatment amount of Product R in a sterile injectable formulation.

2. The method of claim 1 in which an effective treatment amount of Product R is in a range from about 5 microliters to about 40 microliters per kilogram of body weight per day in a sterile injectable formulation.

3. The method of claim 1 in which an effective treatment amount of Product R is in a range from about 10 microliters to about 25 microliters per kilogram of body weight per day in a sterile injectable formulation.

4. The method of claim 1 in which an effective treatment amount of Product R is about 30 microliters per kilogram of body weight per day in a sterile injectable formulation for about one week, followed by about 15 microliters per kilogram of body weight per day in a sterile injectable formulation until said patient becomes asymptomatic or viral load becomes undetectable.

5. A method of treating a patient infected by or carrying the B19 parvovirus, comprising administering parenterally to said patient an effective B19 parvovirus treatment amount of Product R in a sterile injectable formulation.

6. The method of claim 5 in which an effective treatment amount of Product R is in a range from about 5 microliters to about 40 microliters per kilogram of body weight per day in a sterile injectable formulation.

7. The method of claim 5 in which an effective treatment amount of Product R is in a range from about 10 microliters to about 25 microliters per kilogram of body weight per day in a sterile injectable formulation.

8. The method of claim 5 in which an effective treatment amount of Product R is about 30 microliters per kilogram of body weight per day in a sterile injectable formulation for about one week, followed by about 15 microliters per kilogram of body weight per day in a sterile injectable formulation until said patient becomes asymptomatic or viral load becomes undetectable.

9. A method of treating a patient having antibodies to the B19 parvovirus, comprising administering parenterally to said patient an effective B19 parvovirus treatment amount of Product R in a sterile injectable formulation.

10. The method of claim 9 in which an effective treatment amount of Product R is in a range from about 5 microliters to about 40 microliters per kilogram of body weight per day in a sterile injectable formulation.

11. The method of claim 9 in which an effective treatment amount of Product R is in a range from about 10 microliters to about 25 microliters per kilogram of body weight per day in a sterile injectable formulation.

12. The method of claim 9 in which an effective treatment amount of Product R is about 30 microliters per kilogram of body weight per day in a sterile injectable formulation for about one week, followed by about 15 microliters per kilogram of body weight per day in a sterile injectable formulation.

* * * * *